United States Patent [19]
Hoffman

[11] Patent Number: 6,115,448
[45] Date of Patent: Sep. 5, 2000

[54] PHOTODIODE ARRAY FOR A SCALABLE MULTISLICE SCANNING COMPUTED TOMOGRAPHY SYSTEM

[75] Inventor: David M. Hoffman, New Berlin, Wis.

[73] Assignee: General Electric Company, Milwaukee, Wis.

[21] Appl. No.: 08/978,805

[22] Filed: Nov. 26, 1997

[51] Int. Cl.⁷ ........................................ A61B 6/03
[52] U.S. Cl. ............................. 378/19; 378/98.8
[58] Field of Search ................... 378/19, 4, 98.8

[56] References Cited

U.S. PATENT DOCUMENTS

| | | | |
|---|---|---|---|
| 4,365,339 | 12/1982 | Pavkovich et al. | 378/15 |
| 4,965,726 | 10/1990 | Heuscher et al. | |
| 5,430,784 | 7/1995 | Ribner et al. | 378/19 |
| 5,487,098 | 1/1996 | Dobbs et al. | 378/19 |
| 5,592,523 | 1/1997 | Tuy et al. | |

*Primary Examiner*—David V. Bruce
*Assistant Examiner*—Michael J. Schwartz
*Attorney, Agent, or Firm*—Armstrong Teasdale; Christian G. Cabou; Phyllis Y. Price

[57] ABSTRACT

A high density semiconductor array for a scalable multislice computed tomography system is described. In one embodiment, the semiconductor array includes a plurality of photodiodes arranged in rows and columns. A scintillator array is optically coupled to the semiconductor array. Each photodiode creates a low level analog output signal representative of the light output of each scintillator. The semiconductor array enables selection of the number of slices of data to be electrically transmitted for each rotation of the CT system.

31 Claims, 7 Drawing Sheets

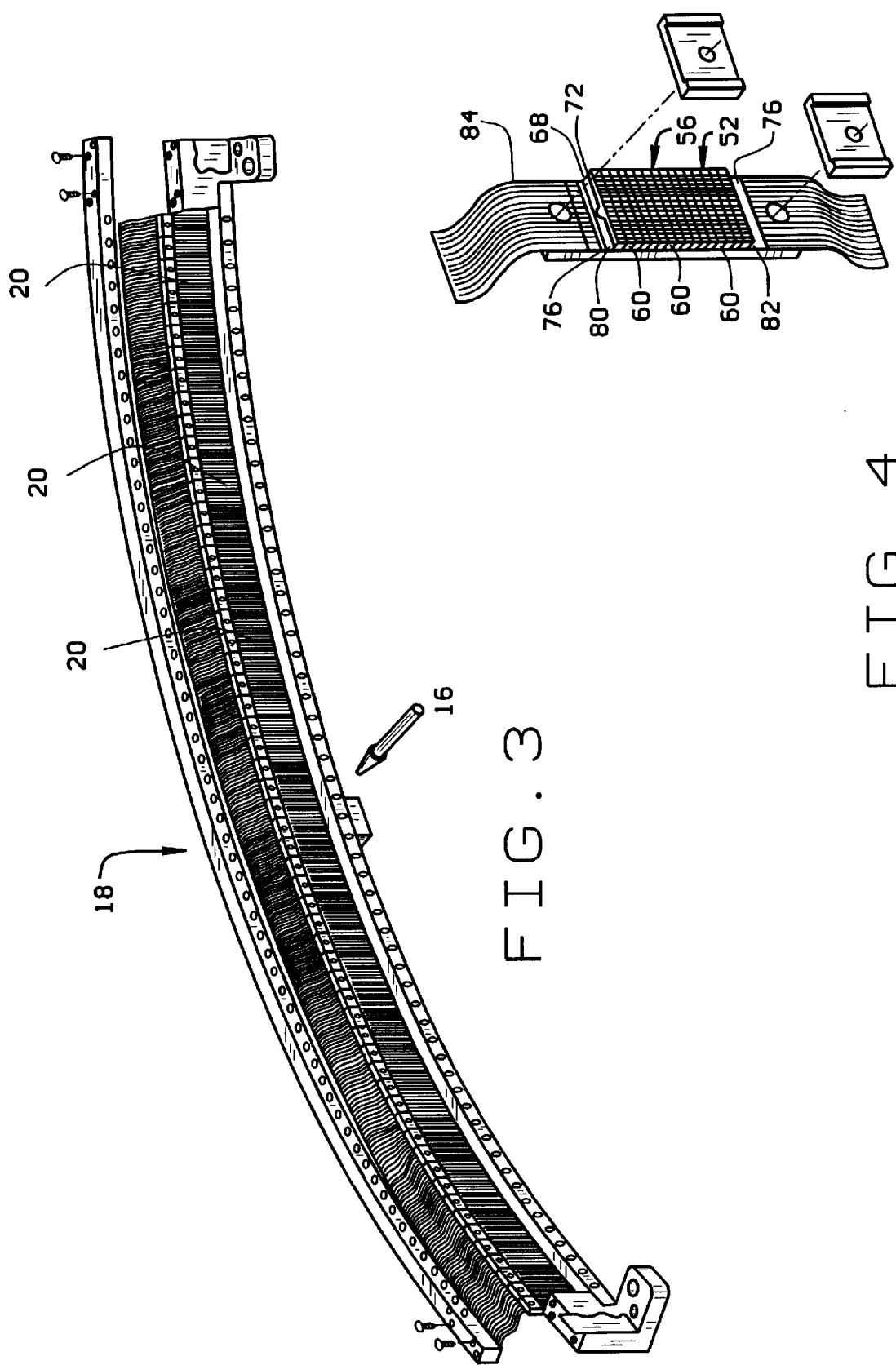

6,115,448

PHOTODIODE ARRAY FOR A SCALABLE MULTISLICE SCANNING COMPUTED TOMOGRAPHY SYSTEM

FIELD OF THE INVENTION

This invention relates generally to computed tomograph imaging and, more particularly, to high density semiconductor arrays utilized in connection with computed tomograph systems.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

Multislice CT systems are used to obtain data for an increased number of slices during a scan. Known multislice systems typically include detectors generally known as 3-D detectors. With such 3-D detectors, a plurality of detector elements form separate channels.

Multislice detectors generate much more data than single slice detectors. This increased data generation capability is not, however, always required or desired. For example, a variety of tests performed by a CT system do not require high slice quantity or high slice resolution. Also, with such large amounts of data being collected, the time required to perform a scan may increase, resulting in higher costs and lower throughput.

Accordingly, it would be desirable to provide a high density semiconductor array that allows data to be transmitted from an alterable number of slices to accommodate the specific needs of a test. In addition, it is desirable to provide a semiconductor array having an alterable slice resolution.

SUMMARY OF THE INVENTION

These and other objects may be attained by a high density semiconductor array which, in one embodiment, generates data signals for a preselected number of slices and slice resolution, or slice thickness. Particularly, the semiconductor array includes a plurality of photodiodes arranged in rows and columns. A scintillator array is optically coupled to the semiconductor array. Each photodiode creates a low level analog output signal representative of the light output of each scintillator. Data is created for a preselected number of slices and slice resolutions by selectively combining output signals from various rows of photodiodes.

In one embodiment, the semiconductor array is fabricated by depositing, or forming an array of photodiodes on a substrate. Output lines from the photodiode array are electrically connected to the data acquisition system to convert the output signals to digital signals for subsequent processing.

The above described semiconductor array enables selection of the number of slices of data to be electrically transmitted for each rotation of the CT system. In addition, the semiconductor array allows the slice thickness to be selected to produce various slice resolutions. As a result, the configuration of the semiconductor array can be altered to accommodate the specific needs and requirements of the test.

BRIEF DESCRIPTION OF THE DRAWINGS

FIG. 3 is a perspective view of a CT system detector array.

FIG. 4 is a perspective view of a detector module shown in FIG. 3.

DETAILED DESCRIPTION

Figure 1:
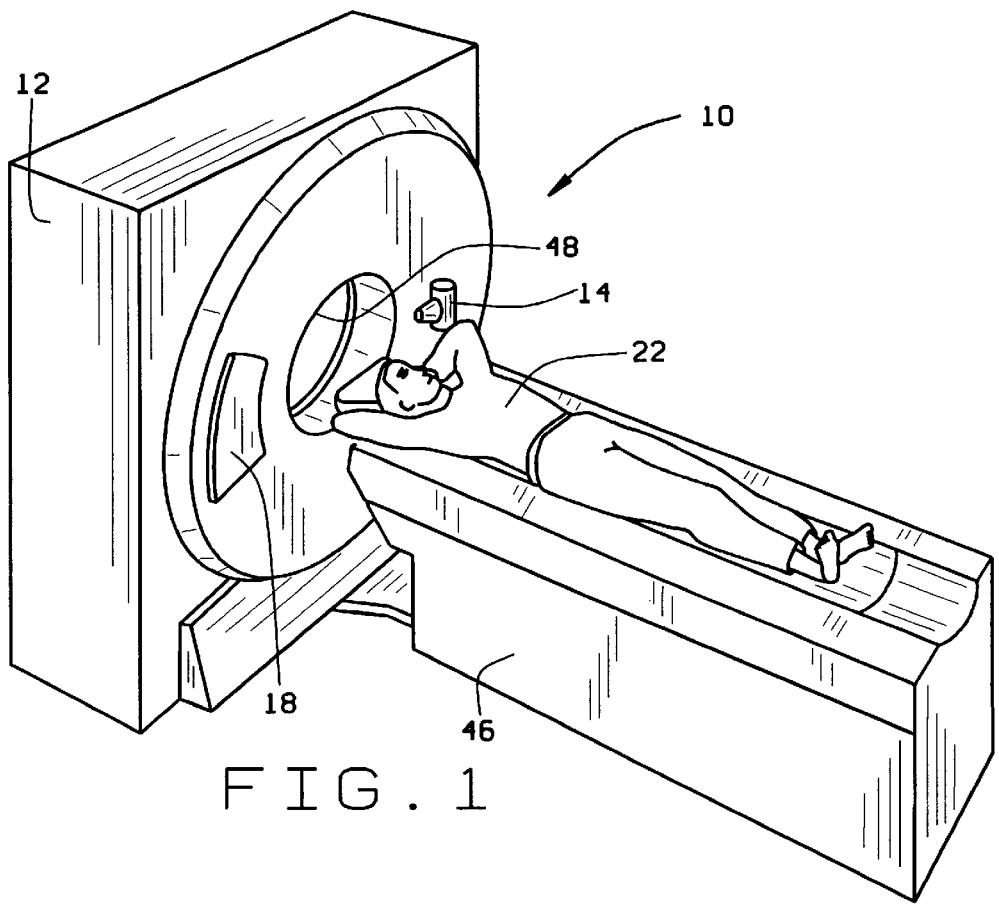
FIG. 1 is a pictorial view of a CT imaging system.
Figure 2:
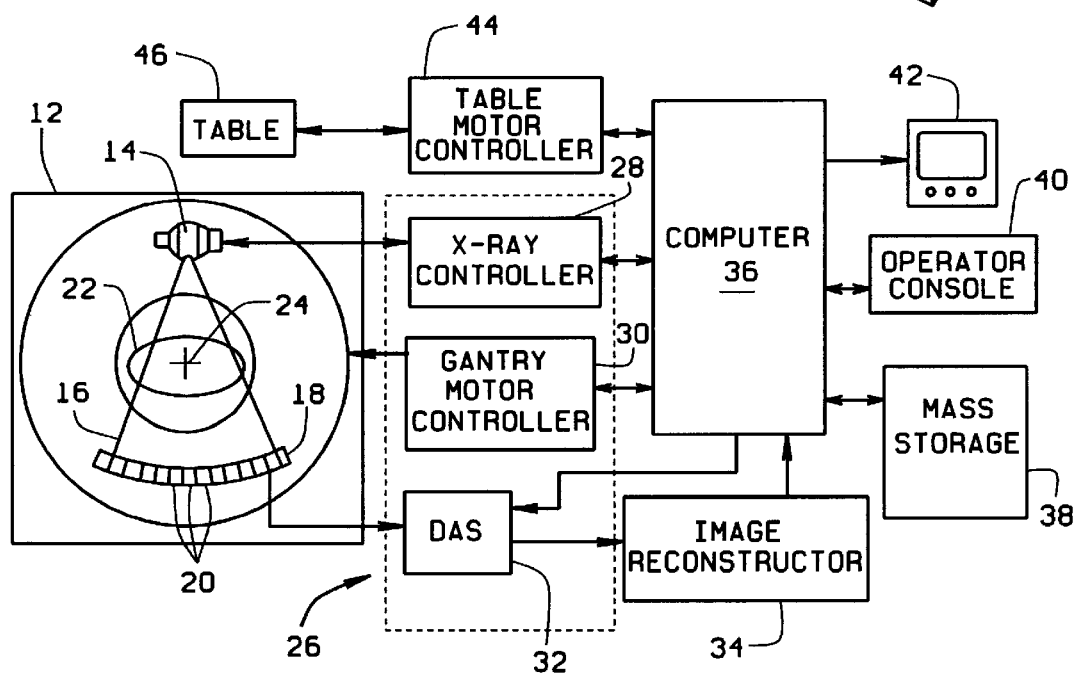
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48.

As shown in FIGS. 3 and 4, detector array 18 includes a plurality of detector modules 20. Each detector module 20 includes a high density semiconductor array 52 and a multidimensional scintillator array 56 positioned above and adjacent to semiconductor array 52. A collimator (not shown) is positioned above and adjacent scintillator array 56 to collimate x-ray beams 16 before such beams impinge upon scintillator array 56. Particularly, semiconductor array 52 includes a plurality of photodiodes 60, a switch apparatus 68, and a decoder 72. Photodiodes 60 may be individual photodiodes or a multi-dimensional photodiode array. Photodiodes 60 are deposited, or formed on a substrate (not shown). Scintillator array 56, as known in the art, is positioned over and adjacent photodiodes 60. Photodiodes 60 are optically coupled to scintillator array 56 and have electrical output lines 76 for transmitting signals representative of the light output by scintillator array 56. Each photodiode 60 produces a separate low level analog output signal that is a measurement of the beam attenuation for a specific scintillator of scintillator array 56. Photodiode output lines 76 may, for example, be physically located on one side of module 20 or on a plurality of sides of module 20. As shown in FIG. 4, photodiode outputs 76 are located at opposing sides of the photodiode array.

In one embodiment, as shown in FIG. 3, detector array 18 includes fifty-seven detector modules 20. Each detector module 20 includes a semiconductor array 52 and scintillator array 56, each having an array size of 16×16. As a result, array 18 has 16 rows and 912 columns (16×57 modules) allowing 16 simultaneous slices of data to be collected with each rotation of gantry 12.

Switch apparatus 68 is a multidimensional semiconductor switch array of similar size as semiconductor array 52. Switch apparatus 68 is coupled between semiconductor array 52 and DAS 32. Semiconductor device 68, in one embodiment, includes two semiconductor switches 80 and 82. Switches 80 and 82 each include a plurality of field effect transistors (FET) (not shown) arranged as a multidimensional array. Each FET includes an input line electrically connected to one of respective photodiode output lines 76, an output line, and a control line (not shown). FET output and control lines are electrically connected to DAS 32 via a flexible electrical cable 84. Particularly, about one-half of photodiode output lines 76 are electrically connected to each FET input line of switch 80 with the other one-half of photodiode output lines 76 electrically connected to the FET input lines of switch 82.

Decoder 72 controls the operation of switch apparatus 68 to enable, disable, or combine photodiode outputs 64 in accordance with a desired number of slices and slice resolutions for each slice. Decoder 72, in one embodiment, is a decoder chip or a FET controller as known in the art. Decoder 72 includes a plurality of output and control lines coupled to switch apparatus 68 and DAS 32. Particularly, the decoder outputs are electrically connected to the switch apparatus control lines to enable switch apparatus 68 to transmit the proper data from the switch apparatus inputs to the switch apparatus outputs. The decoder control lines are electrically connected to the switch apparatus control lines and determine which of the decoder outputs will be enabled. Utilizing decoder 72, specific FETs within switch apparatus 68 are enabled, disable, or combined so that specific photodiode outputs 64 are electrically connected to CT system DAS 32. In one embodiment defined as a 16 slice mode, decoder 72 enables switch apparatus 68 so that all rows of semiconductor array 52 are connected to DAS 32, resulting in 16 simultaneous slices of data are electrically connected to DAS 32. Of course, many other slice combinations are possible.

Figure 5:
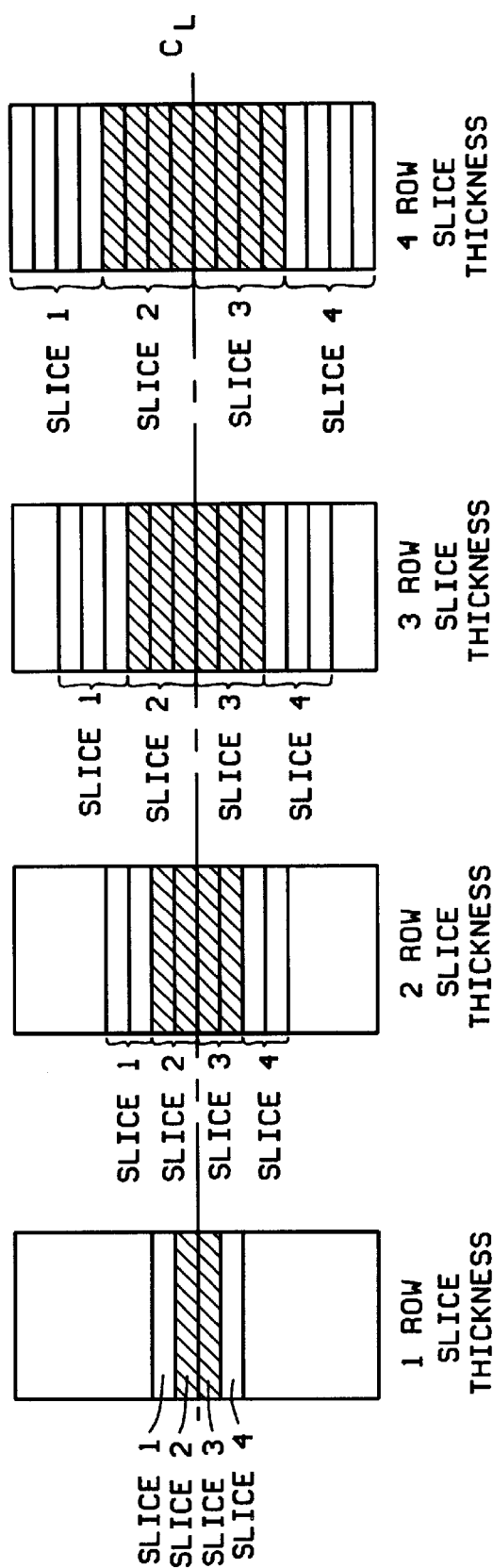
FIG. 5 is illustrative of various configurations of the detector module in FIG. 4 in a four slice mode.

For example, decoder 72 may also select from other multiple slice modes, including one, two, and four slice modes. As shown in FIG. 5, by transmitting the appropriate decoder control lines, switch apparatus 68 can be configured in the four slice mode so that data is collected from four slices of one or more rows of photodiode array 52. Depending upon the specific configuration of switch apparatus 68 as defined by decoder control lines, various combinations of photodiode outputs 64 can be enabled, disabled, or combined so that the slice thickness may consist of 1, 2, 3, or 4 rows of photodiode array elements. Additional examples include, a single slice mode including one slice with slices ranging from 1.25 mm thick to 20 mm thick; and a two slice mode including two slices with slices ranging from 1.25 mm thick to 10 mm thick. Additional modes beyond those described are possible.

Figure 6:
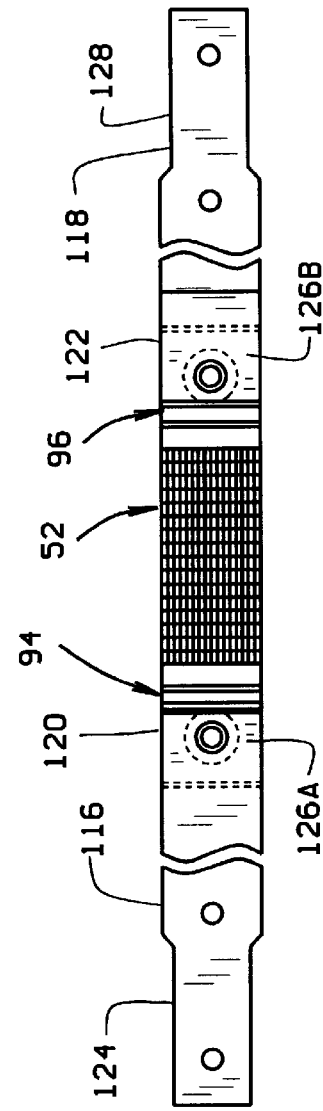
FIG. 6 is a top view of a detector module shown in FIG. 4.
Figure 7:
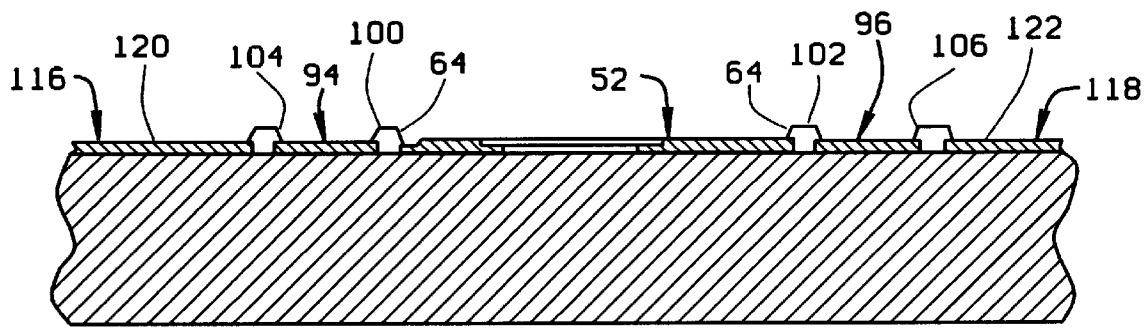
FIG. 7 is a side view of a portion of the detector module shown in FIG. 6.

In one embodiment, switch apparatus 68 and decoder 72 are combined into a FET array 90. FET array 90 includes a plurality of field effect transistors (FET) (not shown) arranged as a multidimensional array. In one embodiment and referring to FIGS. 6 and 7, two semiconductor devices 94 and 96 are utilized so that one-half of photodiode output lines 64 are connected to device 94 and one-half of photodiode output lines 64 are connected to device 96. FET arrays 94 and 96 each include respective input lines 100 and 102, output lines 104 and 106, and control lines (not shown). Internal to device 94, input lines 100 are electrically connected to the switch apparatus input lines, output lines 104 are electrically connected to the switch apparatus output lines, and decoder output lines are electrically connected to FET control lines. Switch 96 is internally configured identical to switch 94.

Flexible electrical cable 84 includes a first end (not shown), a second end (not shown) and a plurality of electrical wires 112 traveling therebetween. Cable 84 may, for example, be two cables 116 and 118 having respective first ends 120 and 122 and respective second ends 124 and 128 or in an alternative embodiment, may include a single cable (not shown) having multiple first ends (not shown). In one embodiment, the FET output and control lines of FET array 94 are connected to wires 112 of cable 116, and the FET output and control lines of FET array 96 are connected to wires 112 of cable 118. Particularly, each FET output and control line is electrically connected to a wire 112 of respective cable first ends 120 and 122. Respective cable first ends 120 and 122 are held in firm electrical contact with the FETs by mounting brackets 126A and 126B.

Figure 8:
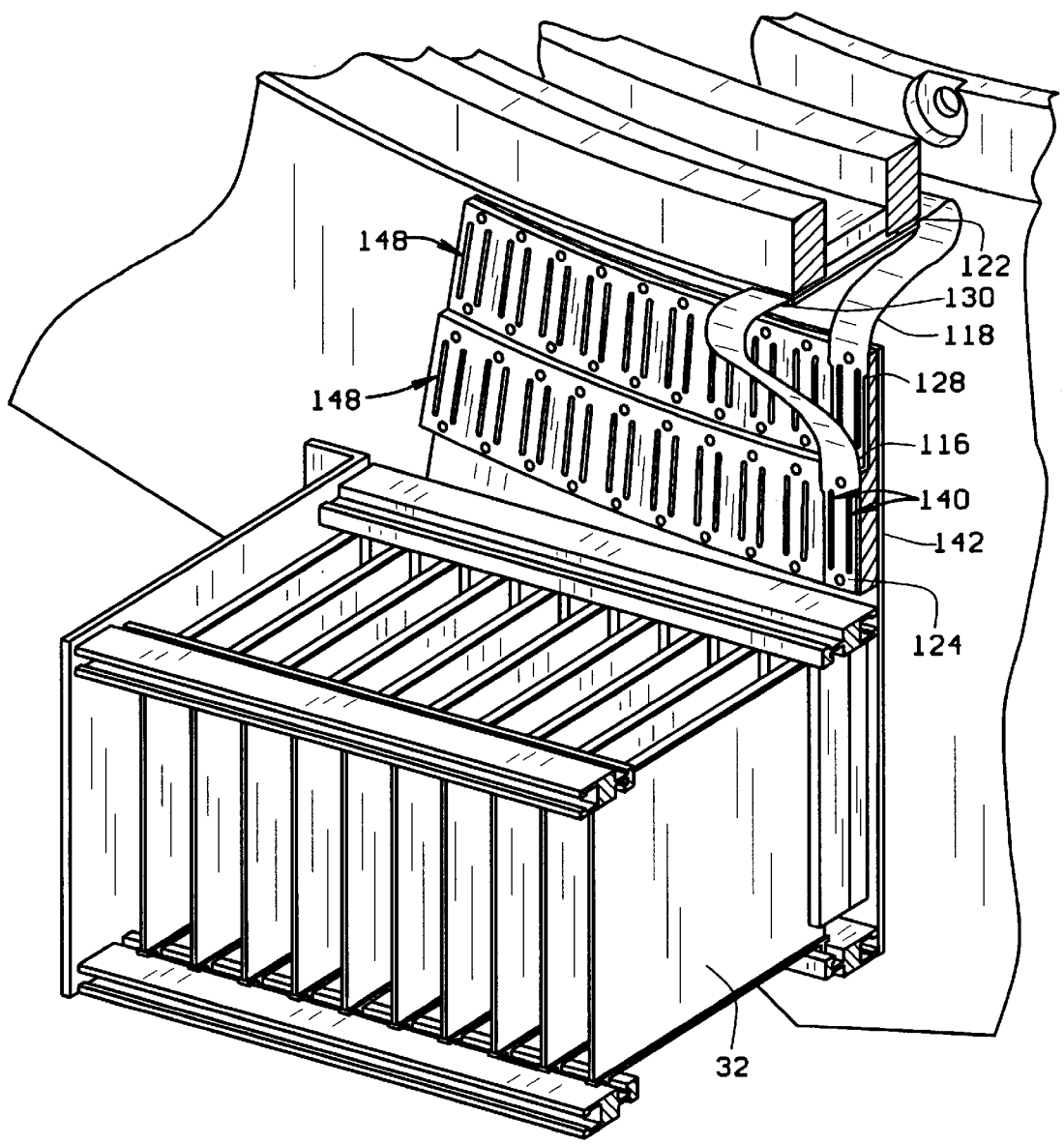
FIG. 8 is a perspective view of a detector module to data acquisition system interconnection prior to securing of a housing.
Figure 9:
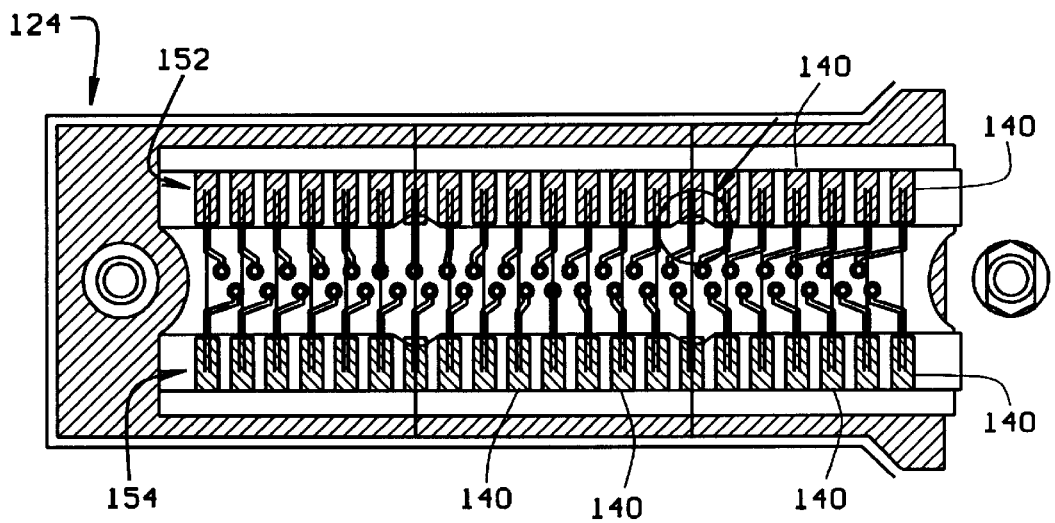
FIG. 9 is an enlarged top view of the flexible cable second end shown in FIG. 8.
Figure 10:
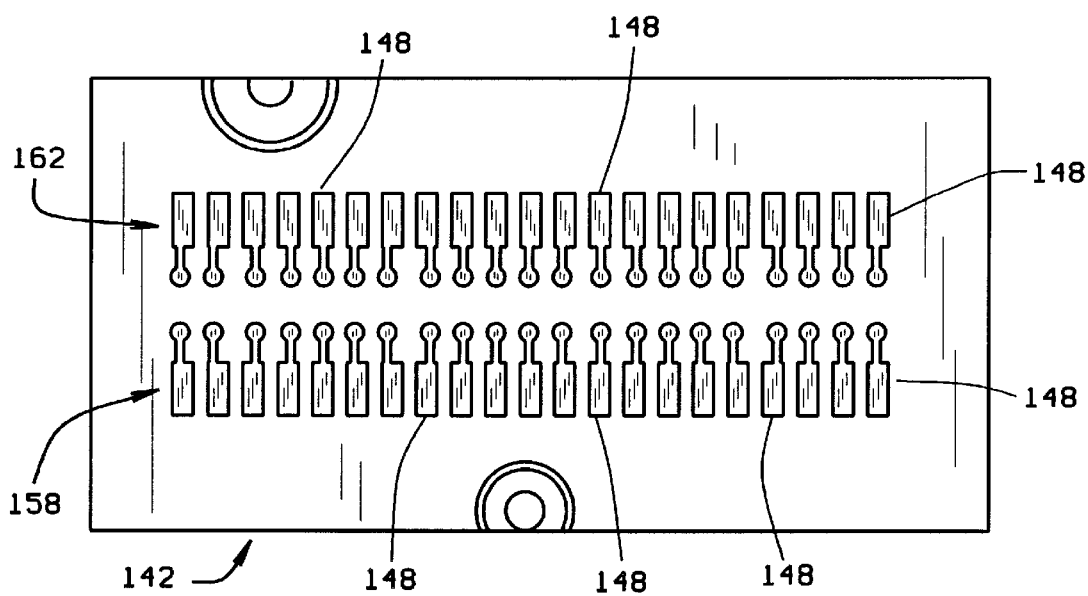
FIG. 10 is an enlarged top view of the backplane connection pads.

In one embodiment and referring to FIGS. 8, 9 and 10, cables 116 and 118 are identical. Referring specifically to cable 116, second end 124 includes a plurality of connection pads 140 arranged in a pattern. Each connection pad 140 is electrically connected to a wire 112 at cable second end 124. Cable second end 124 is electrically coupled to a DAS backplane 142 utilizing an elastomeric connector (not shown in FIGS. 7, 8 and 9). Backplane 142 includes a plurality of connection pads 148 arranged in a pattern identical to connection pads 140. Backplane connection pads 148 are electrically connected to DAS input and control lines (not shown). In one embodiment, connection pads 140 are arranged in a pattern having two parallel rows 152 and 154, connection pads 148 are similarly laid out having two parallel rows 158 and 162, and two elastomeric connectors (not shown) are utilized to electrically connect connection pads 140 and 148. Each elastomeric connector includes a plurality of conductors (not shown) aligning with the connection pads so that positioning the elastomeric connectors between cable second end 124 and backplane 142 electrically connects connection pads 140 and 148. Particularly, the first elastomeric connector is positioned between connection pad rows 152 and 158, and the second elastomeric connector is positioned between connection pad rows 154 and 162. Cable second end 124 is secured to backplane 142 with a housing (not shown). Cable 118 is connected to backplane 142 in a similar manner.

Figure 11:
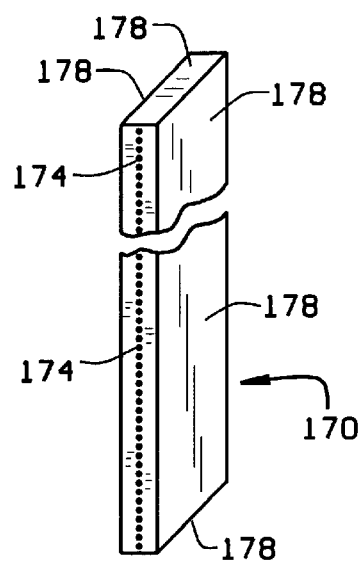
FIG. 11 is perspective view of the elastomeric connector with a portion of the insulating material removed.

Referring to FIG. 11, elastomeric connector 170 includes at least one conductor 174 surrounded on all sides by an insulating material 178. Ends of the elastomeric connector are not covered with insulating material 178 so that conductor 174 may make electrical connection with pads 140 and 148. In one embodiment, elastomeric connector 170 includes a plurality of gold plated brass conductors 174. Conductors 174 may be spaced so that a single conductor 174 makes electrical connection between each connection pad 140 and each connection pad 148. Alternatively, conductors 174 may be spaced so that a plurality of conductors 174 make electrical connection between each connection pad 140 and each connection pad 148.

Figure 12:
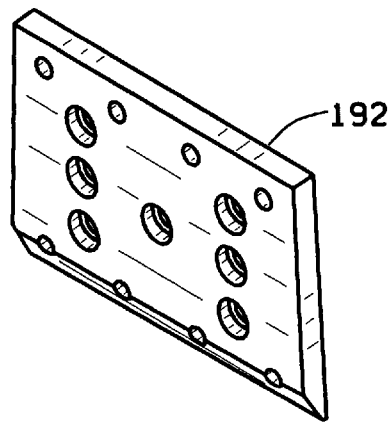
FIG. 12 is a perspective view of the housing for securing the connector to the backplane.

In one embodiment and referring to FIG. 12, a housing 192 fits over a plurality of cable second ends and is secured to backplane 142. Particularly, housing 192 compresses elastomeric connector 170 between flexible cable second end 124 and backplane 142 so that electrical connections are made by connection pads 140 and 148 via elastomeric conductors 174. As a result, output lines 76 are electrically coupled to the backplane input lines and the FET control lines are connected to the DAS control lines to configure detector module semiconductor switches 80 and 82. Housing 192 is secured to backplane 142 using at least one bolt (not shown).

Figure 13:
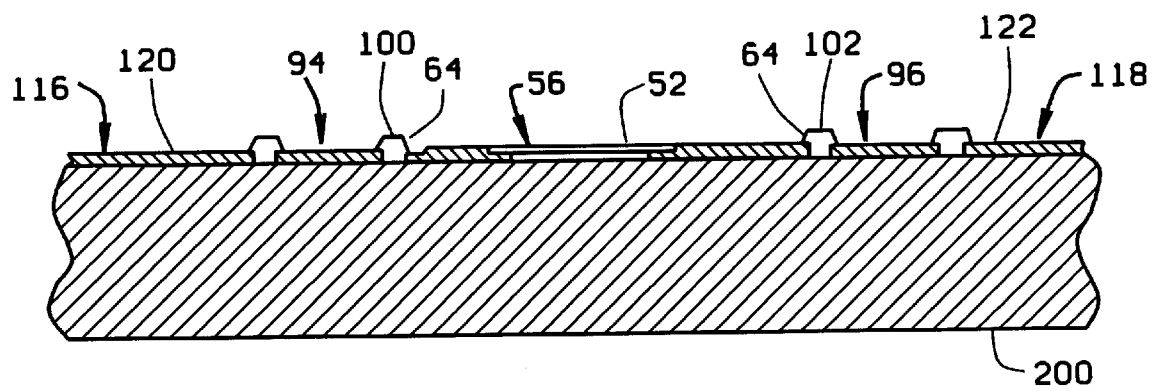
FIG. 13 is a side view of a portion of the detector module shown in FIG. 4.

In fabrication of detector module 20 and referring to FIG. 13, semiconductor array 52 including scintillator array 56 and FET arrays 94 and 96 are deposited, or formed, on substrate 200 in a manner known in the art so that photodiodes 60 are positioned adjacent and between arrays 94 and 96. Photodiode outputs 64 are then connected to inputs 100 and 102 of respective FET arrays 94 and 96. Particularly, one-half of photodiode outputs 64 are wire bonded to FET array inputs 100 and one-half of photodiode outputs 64 are wire bonded to respective FET array inputs 102 so that each output 64 is electrically connected to a FET input line. Photodiode outputs are wire bonded to FET input lines using various wire bonding techniques, including, for example, aluminum wire wedge bonding and gold wire ball bonding as known in the art.

Respective cable first ends 120 and 122 are positioned adjacent to respective FET arrays 94 and 96 and coupled to substrate 200 using, for example, an adhesive (not shown). A portion of the FET output and control lines are then wire bonded to wires 112 of cable 116 and a portion of the FET output and control lines are wire bonded to wires 112 of cable 118 so that an electrical path is created between each FET output line and a wire 112 and each FET control line and a wire 112. FET output and control lines are wire bonded similar to photodiode output lines 64, wire bonds are generally identified as bonds 300. Cable first ends 120 and 122 are maintained in place using mounting brackets 126A and 126B.

After mounting detector modules 20 into detector array 18, cable second ends 124 and 128 are coupled to DAS 32 so that an electrical path exists between the photodiode output lines 76 and the DAS inputs, and the FET control lines are electrically connected to the DAS outputs to enable FET arrays. Particularly, a first end of elastomeric connector 170 is positioned adjacent backplane 142 so that elastomeric conductors 174 are positioned adjacent connection pads 148. Flexible cable second end 124 is then positioned adjacent a second end of elastomeric connector 170 so that elastomeric conductors 174 are positioned adjacent connection pads 140. After positioning housing 192 over and adjacent cable second end 124, housing 192 is secured to backplane 142 until elastomeric connector 170 is compressed so that elastomeric conductors 174 are electrically connected to cable second end connection pads 140 and backplane connection pads 148.

In operation, the operator determines the number of slices and thickness of each slice. The appropriate configuration information is transmitted to the array control lines to configure switch apparatus 68 using decoder 72. As X-ray beams 16 impinge upon detector modules 20, data for the selected configuration is transmitted to DAS 32.

The above described semiconductor array enables selection of the number of slices of data to be electrically transmitted for each rotation of the CT system. In addition, the semiconductor array allows the slice thickness to be selected to produce various slice resolutions. As a result, the configuration of the semiconductor array can be altered to accommodate the specific needs and requirements of the test.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

I claim:

1. A high density semiconductor array for a multislice computed tomograph machine, said array comprising:
    a plurality of photodiodes configured as a photodiode array having electrical outputs; and
    a scintillator array optically coupled to said photodiode array; and
    a switch electrically coupled to said photodiode array outputs.

2. A high density semiconductor array in accordance with claim 1 wherein said scintillator array and said photodiode array are 16×16 arrays.

3. A multislice detector for a computed tomograph machine, said detector comprising:

a detector housing;

a plurality of detector modules coupled to said detector housing, said detector modules selectively configurable to generate outputs in accordance with a preselected number of slices and slice thickness and to operate in a plurality of slice modes;

a collimator array adjacent said detector modules; and a backplane electrically coupled to outputs of said detector modules.

4. A high density semiconductor array in accordance with claim 3 wherein said switch comprises a plurality of field effect transistors.

5. A high density semiconductor array in accordance with claim 4 wherein each of said field effect transistors are wire bonded to one of said photodiode outputs.

6. A high density semiconductor array in accordance with claim 3 wherein said switch comprises an array of field effect transistors.

7. A high density semiconductor array in accordance with claim 3 wherein said photodiode array and said switch are on a substrate.

8. A high density semiconductor array in accordance with claim 3 further comprising a decoder coupled to said switch, said decoder configured to control operation of said switch to combine said photodiode array outputs in accordance with a preselected number of slices and slice thickness.

9. A high density semiconductor array in accordance with claim 8 wherein said decoder controls said switch to selectively operate in a plurality of slice modes.

10. A detector module for a computed tomograph machine, said detector module comprising:

a high density semiconductor array comprising a plurality of photodiodes and having outputs;

a scintillator array optically coupled to said high density semiconductor array;

at least one flexible cable electrically connected at one end to outputs of said high density semiconductor array; and a switch electrically coupled between said high density semiconductor array outputs and said at least one flexible electrical cable.

11. A detector module in accordance with claim 10 wherein said switch is wire bonded to said high density semiconductor array and said at least one flexible cable.

12. A detector module in accordance with claim 10 wherein said switch comprises a plurality of field effect transistors.

13. A detector module in accordance with claim 12 wherein said at least one flexible electrical cable comprises a plurality of electrical wires, and each of said field effect transistors electrically connected to one of said electrical wires.

14. A detector module in accordance with claim 10 wherein said high density semiconductor array and said scintillator arrays are 16×16 arrays.

15. A multislice detector for a computed tomograph machine, said detector comprising:

a detector housing;

a plurality of detector modules coupled to said detector housing, said detector modules selectively configurable to generate outputs in accordance with a preselected number of slices and slice thickness; and a collimator array adjacent said detector modules.

16. A multislice detector in accordance with claim 15 further comprising a backplane electrically coupled to outputs of said detector modules.

17. A multislice detector in accordance with claim 16 wherein each said detector module comprises at least one flexible electrical cable, wherein each of said electrical cables is electrically coupled between each of said detector modules and said backplane.

18. A multislice detector in accordance with claim 17 further comprising at least one elastomeric connector electrically connecting one end of each of said electrical cables to said backplane.

19. A multislice detector in accordance with claim 18 wherein said backplane comprises a plurality of inputs, wherein one end of each of said flexible cables and each input of said backplane comprise a connection pad, and wherein said connection pads are configured to electrically couple to said elastomeric connector.

20. A multislice detector in accordance with claim 19 wherein said elastomeric connector comprises a plurality of silver impregnated silicone layer conductors.

21. A multislice detector in accordance with claim 19 wherein said elastomeric connector comprises a plurality of gold plated brass or nickel conductors.

22. A multislice detector in accordance with claim 15 wherein said detector modules operate in a plurality of slice modes.

23. A multislice detector in accordance with claim 22 wherein one of said slice modes is a four slice mode, and for said four slice mode, a selected slice thickness comprises at least one row.

24. A multislice detector in accordance with claim 3 wherein one of said slice modes is a four slice mode, and for said four slice mode, a selected slice thickness comprises at least one row.

25. A multislice detector in accordance with claim 3 wherein each said detector module comprises at least one flexible electrical cable, wherein each of said electrical cables is electrically coupled between each of said detector modules and said backplane.

26. A multislice detector in accordance with claim 25 further comprising at least one elastomeric connector electrically connecting one end of each of said electrical cables to said backplane.

27. A multislice detector in accordance with claim 26 wherein said backplane comprises a plurality of inputs, wherein one end of each of said flexible cables and each input of said backplane comprise a connection pad, and wherein said connection pads are configured to electrically couple to said elastomeric connector.

28. A multislice detector in accordance with claim 16 wherein said detector modules comprise high density semiconductor arrays each having a plurality of photodiodes configured as an array and a scintillator array optically coupled to said photodiode array.

29. A multislice detector in accordance with claim 28 wherein said photodiode array has photodiode array outputs, and said high density semiconductor array further comprises a switch electrically coupled to said photodiode array outputs.

30. A multislice detector in accordance with claim 29 wherein said switch comprises a plurality of field effect transistors.

31. A multislice detector in accordance with claim 28 further comprising a decoder coupled to said switch, said decoder configured to control operation of said switch to combine said photodiode array outputs in accordance with a preselected number of slice and slice thicknesses.

* * * * *